Figure 1:
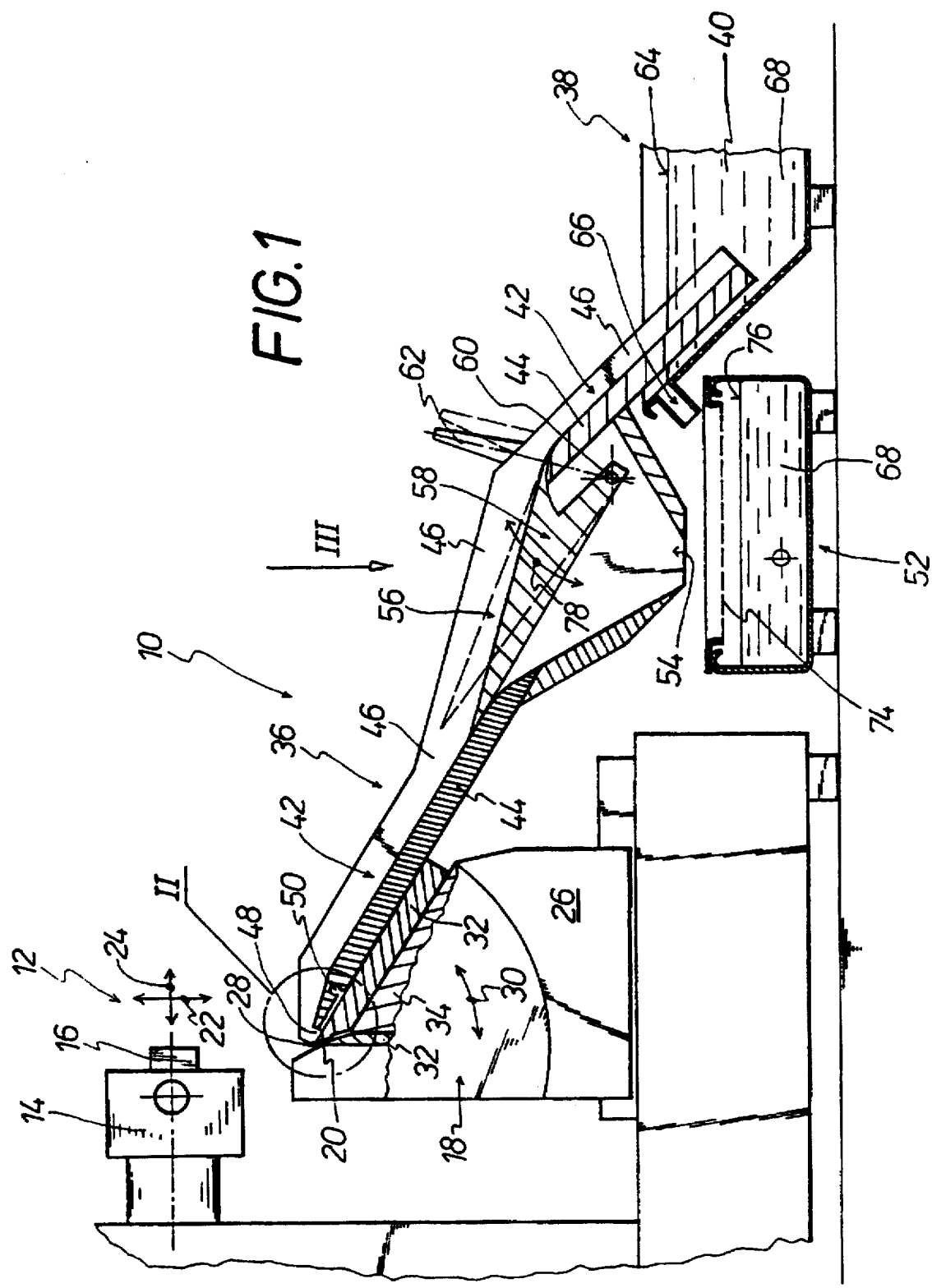

United States Patent

Izvozichikov et al.

Patent Number: 5,713,255
Date of Patent: Feb. 3, 1998

[54] PROCESS AND APPARATUS FOR THE PRODUCTION OF THIN SECTIONS BY MEANS OF A MICROTOME

[75] Inventors: Ilia Borisovitch Izvozichikov; Serquei Petrovitch Mikhailov, both of St. Petersburg, Russian Federation

[73] Assignee: Microm Laborgerate GmbH, Walldorf, Germany

[21] Appl. No.: 356,409

[22] PCT Filed: Jul. 5, 1993

[86] PCT No.: PCT/DE93/00598

§ 371 Date: Feb. 14, 1995

§ 102(e) Date: Feb. 14, 1995

[87] PCT Pub. No.: WO94/01751

PCT Pub. Date: Jan. 20, 1994

[30] Foreign Application Priority Data

Jul. 10, 1992 [RU] Russian Federation ............ 5.055.244

[51] Int. Cl.⁶ ................................................ G01N 1/06
[52] U.S. Cl. ................................ 83/24; 83/98; 83/111; 83/106; 83/167; 83/915.5; 83/703
[58] Field of Search ............................. 83/22, 24, 98, 83/111, 167, 169, 170, 171, 102, 106, 105, 915.5, 703, 707, 713, 23

[56] References Cited

U.S. PATENT DOCUMENTS 2,292,973  8/1942  Richards ........................ 83/169 X
3,103,844  9/1963  Persson ........................... 83/167 X
3,191,476  6/1965  McCormick .
3,225,639  12/1965  Martinelli ...................... 83/915.5 X
3,540,335  11/1970  Sitte ............................. 83/915.5 X
3,552,247  1/1971  Pickett .
3,667,330  6/1972  Kobernick ....................... 83/915.5 X
3,680,420  8/1972  Blum ............................. 83/167 X
4,051,755  10/1977  Raveed .......................... 83/168 X
4,083,277  4/1978  Lotz ............................. 83/106 X
4,447,952  5/1984  Elkins ........................... 83/170 X
5,048,300  9/1991  Lihl .............................. 83/171 X

FOREIGN PATENT DOCUMENTS 2200415  7/1973  Germany .

*Primary Examiner*—Rinaldi I. Rada
*Assistant Examiner*—Boyer Ashley
*Attorney, Agent, or Firm*—Bachman & LaPointe P.C.

[57] ABSTRACT

Described is a process and an apparatus (10) for the production of thin sections which are cut off a specimen (16), by the use of a cutting blade (20) of a microtome (12), and then transferred to a liquid bath (40). In order to prevent undesired compression of thin sections (98) during the cutting operation, the thin sections (98) are transfer from the cutting blade (20) to the liquid bath (40) by flowing fluid from the cutting blade (20) to the liquid bath, wherein the liquid bath is disposed at a spacing from the cutting blade by a flow passage. The flowing fluid is selectively guided, by a change-over switching device (56), to the liquid bath (40) or to a waste container (52) so that good thin sections (98) are separated from unsatisfactory thin sections (98).

19 Claims, 7 Drawing Sheets

PROCESS AND APPARATUS FOR THE PRODUCTION OF THIN SECTIONS BY MEANS OF A MICROTOME

The invention relates to a process for the production of thin sections which, by means of a cutting blade of a microtome, are cut off a thin-section specimen held by means of a specimen holder of the microtome, and which are transferred to a liquid bath, and an apparatus for carrying out that process, which has a cutting blue and a specimen holder provided for a thin-section specimen from which a thin section is to be cut, the cutting blade and the specimen holder being movable relative to each other, a liquid bath being provided to receive the corresponding thin sections.

Such a process and an apparatus for carrying out the process are known from German patent specification No 22 00 415. In that process and apparatus the liquid bath directly adjoins the cutting edge of the cutting blade, with the liquid being in the rest condition; that however does not exclude the possibility of the individual thin sections suffering from a certain degree of buckling or upsetting, even if only relatively slight, in particular in the transitional region between the cutting edge of the cutting blade and the calm surface of the bath. In order to provide that the individual thin sections are transported away from the cutting blade, in an improved fashion in comparison with known microtomes which have a thin section-removal device of band-like nature, it is additionally necessary for the cutting blade to be provided with a cooling device and for the liquid container which contains the liquid to be provided with a heating device, in order to adjust the liquid to a given temperature. As the cooling device and the heating device the disposed relatively close together, not only does not that arrangement require suitable thermal insulation, but in addition it involves an amount of expenditure of energy for the cooling and heating devices, which is not negligible. A further disadvantage of that known apparatus is that the calm liquid bath receives not only the thin sections which are referred to as good thin sections, but also the unsatisfactory thin sections which are produced for example between those good thin sections and which represent wastage that cannot be put to use. That means however that operation with such a known microtome still leaves something to be desired.

An object of the present invention is to provide a process and an apparatus of the kind set forth in the opening part of this specification, wherein, while involving a low level of structure expenditure and using a comparatively small amount of energy, undesirable compression of the individual thin sections is avoided, and at the same time a section-stretching action is produced in a simple fashion, in respect of the individual thin sections.

In regard to the process, that object is attained in that the transfer of the thin sections from the cutting blade to the liquid bath is effected by a fluid flowing from the cutting blade to the liquid bath which is spaced from the cutting blade. The fluid which flows between the cutting blade or between the vicinity of the cutting edge of the cutting blade and the liquid bath produces, immediately adjoining the cutting operation, a transportation force which acts on the individual thin sections and with which said thin sections are transported away from the cutting edge of the cutting blade to the liquid bath, while at the same time the flowing fluid causes a stretching effect in respect of the individual thin sections. At the same time, that advantageously prevents undesired compression of the individual thin sections or corresponding portions thereof.

In that respect it has been found to be particularly advantageous if transfer of the thin sections from the cutting blade or from the cutting edge of the cutting blade of the microtome to the liquid bath is effected by means of a fluid which flows with a laminar flow. Such a laminar flow of said fluid produces an optimum stretching action in respect of the individual thin sections and consequently provides for avoiding compression thereof, so that undesirable buckling deformation of the individual thin sections is avoided.

The above-mentioned fluid for transporting the thin sections from the cutting blade to the liquid bath may be a gas forming a transportation cushion along which the individual thin sections are transported from the cutting edge of the cutting blade to the liquid bath. It is advantageous however if the fluid used is the liquid of the liquid bath. In that case the bath liquid is simply transported in a closed circuit between the vicinity of the cutting edge of the cutting blade and the liquid bath, and from there back into the vicinity of the cutting edge of the blade. That advantageously minimises any possible loss or wastage of liquid.

It has been found particularly advantageous if, in the process according to the invention, the fluid is selectively diverted to the liquid bath or to a waste container by means of a change-over switching device. In that way it is easily possible for only so-called good thin sections to be guided into the liquid bath, while unsatisfactory, that is to say non-good, thin sections such as the initial cuts from a specimen or sections produced by coarse feed movements, or unsatisfactory thin sections which are produced between so-called good thin sections, can simply be guided into the waste container. In that respect, establishing whether a thin section is good or unsatisfactory can easily be effected in an advantageous fashion along the path of movement between the cutting edge of the cutting blade and the liquid bath, that is to say along the path of movement along which the corresponding thin sections are transported by means of the flowing fluid. By suitable choice of the speed of flow of the flowing fluid and by suitable choice of the length of the fluid flow path, that is to say by suitable choice of the spacing between the cutting blade and the liquid bath, it is possible for the residence time of the individual thin sections to be made sufficiently long for optical investigation thereof, so that the individual thin sections can be passed either to the liquid bath or to the waste container, by means of the above-mentioned switching device. In contrast to the microtome known from above-mentioned German patent specification No 22 00 415, in which, for the purposes of distinguishing between good thin sections and coarse initial cuts from a specimen, it is necessary for the specimen holder to be laterally displaced relative to the cutting blade in order to associate it either with the liquid bath or with a region laterally beside the liquid bath, it is not necessary in accordance with the invention to provide for a corresponding lateral displacement as between the specimen holder and the cutting blade of the microtome. That however means that the degree of precision of the thin section work in accordance with the invention is also advantageously improved.

In accordance with the invention, in order to be able to produce a very wide range of materials such as histological thin-section specimens which are embedded in wax, or thin-section specimens of synthetic resins or plastics mixtures, in a very wide range of wall thicknesses of for example 1 µm, or even considerably thicker thin sections, without involving a compression effect and without buckling deformation, it is desirable if, in accordance with the invention, the amount of fluid and/or the speed of the fluid is suitably adjusted downstream of the cutting blade. In that respect, the rough calculation that applies may be as follows: the greater the thickness of the thin sections, the greater should be in particular the amount of fluid which flows per unit of time from the vicinity of the cutting edge of the cutting blade to the liquid bath or to the waste container. The speed of flow of the fluid is dependent in particular on the cutting speed at which a thin section is cut from the thin-section specimen. Here the following rough formula may apply: the greater the cutting speed, the greater should be the fluid speed in order to produce a suitable stretching effect.

When producing individual thin sections which are separated from each other in respect of time, it can repeatedly be found that the individual thin sections remain caught by their rearward or trailing edge, at the cutting edge of the cutting blade. The same effect can be observed if thin sections are produced in immediate succession, which then form what is called a thin-section strip. In the last-mentioned case, it frequently happens that the last thin section remains caught by its rearward or trailing edge, at the cutting edge of the cutting blade. That however has an adverse effect on the cutting operation. In order to eliminate that adverse effect, it has been found advantageous if release of the rearward or trailing edge of the thin section or the respective last thin section of a thin-section strip or series is effected by means of a release device which is disposed beside the cutting blade and which is adjustable in relation to the cutting edge of the cutting blade. The release device can be actuated manually or by means of a suitable drive device. The same applies in regard to the above-mentioned change-over switching device for the fluid for transporting the thin sections from the cutting blade to the liquid bath or to the waste container respectively; it can also guide the fluid selectively to the liquid bath or to the waste container, manually or by means of a suitable drive device.

In regard to the apparatus, the above-indicated object of the invention is achieved in that the liquid bath is disposed at a spacing from the cutting blade, and that provided between the cutting blade and the liquid bath is a flow passage or duct for a fluid, by means of which the thin sections are or can be transported from the cutting edge of the cutting blade to the liquid bath, wherein the portion of the cutting blade which adjoins the cutting edge thereof defines a cavity of the flow passage, from which at least a part of the fluid issues and flows into the flow passage. The flow passage between the cutting blade and the liquid bath affords the possibility that the fluid which is transporting the thin sections is guided in a defined manner from the cutting blade or from the cutting edge thereof to the liquid bath, and thereby transports the thin sections in such a way as to avoid compressing them and to produce stretching thereof. At the same time it is possible to examine the individual transported thin sections as they pass along the flow passage, in order to be able to separate so-called good thin sections from unsatisfactory thin sections or initially cut sections which involved a coarse feed movement, or the like. That has the advantage of ensuring that the liquid bath is not encumbered with unsatisfactory thin sections.

A good action in regard to stretching the sections and preventing compression thereof is achieved if the flow passage is provided for an at least approximately laminar flow of the fluid. That can be achieved by the flow passage being of a suitable design configuration. In that respect, downstream of the cavity adjoining the cutting blade or its cutting edge, the flow passage is advantageously formed with a bottom and with two mutually opposite side walls which stand away from the bottom, wherein the bottom and/or the side walls may be provided with additional fluid inlets for selective adjustment of the amount of fluid and/or the speed of flow of the fluid in the flow passage. If necessary it is also possible to omit such fluid inlets, in other words, it may be sufficient for the flow passage to be provided only with the above-mentioned cavity from which the fluid issues into the flow passage, in the vicinity of the cutting edge of the cutting blade. As already stated above, the fluid may be a gas; preferably however the fluid used is a liquid because a suitable liquid makes it possible to provide a good stretching effect for the thin sections. The above-mentioned liquid may be water which can be mixed with suitable additives.

In regard to the apparatus according to the invention, it has been found advantageous if a change-over switching device is provided in the flow passage for selectively diverting the fluid to the liquid bath or to a waste container. The change-over switching device makes it possible for so-called good thin sections to be guided to the liquid bath by means of the fluid in the flow passage, while other thin sections such as unsatisfactory thin sections, initially cut sections which were cut with a coarse feed movement, and the like, are diverted to the waste container. That affords the advantage that in actual fact only so-called good thin sections float on the surface of the liquid in the liquid bath, and from there can be removed in per se known manner.

If the fluid for the flow passage is the liquid of the liquid bath, it is desirable if the liquid bath is provided with an overflow means which opens into the waste container, and the waste container is communicated by means of a return line with the cavity adjoining the cutting blade, wherein a conveyor device for the fluid is provided in the return line. The conveyor device is desirably a conveyor pump. If the flow passage is provided with the additional fluid inlets referred to above, it is desirable if the last-mentioned return line is communicated not only with the cavity disposed in the vicinity of the cutting blade, but also with those fluid inlets. In that case, by means of those fluid inlets, depending on the respective position of the change-over switching device for guiding the fluid to the liquid bath or to the waste container, it is possible deliberately to adjust the flow of the fluid in the flow passage in such a way that the guidance effect of the switching device is increased or enhanced by the said flow of fluid.

Because the liquid bath is provided with an overflow means which opens into the waste container, that arrangement also affords the advantage that the consumption of liquid is relatively slight.

In the apparatus according to the invention, the change-over switching device may have a flap which forms a portion of the bottom of the flow passage and which is pivotable about a pivot axis which is parallel to the bottom of the flow passage. Another possible construction provides that the change-over switching device has a plate or turntable which is pivotable about an axis perpendicular to the bottom of the flow passage, the turntable having a deflection surface which projects from the face thereof. Another possible construction provides that the change-over switching device of the apparatus according to the invention has a deflection finger which is pivotable about an axis of rotation that is perpendicular to the bottom of the flow passage, the deflection finger having two guide surfaces which face away from each other and which stand up out of the flow passage. Irrespective of the specific configuration of the switching device, it is easily possible therewith to guide the flow of fluid away from the cutting blade specifically either to the liquid bath or to the waste container, so that good thin sections are guided to the liquid bath while inadequate or unsatisfactory thin sections, initially cut sections which were cut with a coarse feed movement, or the like, are passed to the waste container.

The bath container may be provided in per se known manner with a heating means in order to provide for heating the liquid in the container; that may be appropriate in particular when dealing with thin-section specimens which are embedded in wax.

To release the rearward or trailing edge of the thin section or the respective last thin section of a series of thin sections, the apparatus may include, disposed beside the cutting blade in the region of the cavity of the flow passage, a release device which is displaceable in relation to the cutting edge of the cutting blade. The release device may be in the form of a blade or knife edge, or it may be in the form of a wire element which is tensioned between two lateral leg portions, or the like, and it can be actuated manually or by means of a drive device. In a corresponding fashion, depending on the desired degree of comfort and convenience in operation of the apparatus according to the invention, the change-over switching device disposed in the flow passage, for controlling the direction of the flow of fluid for transporting the thin sections, can be actuated manually or by a suitable drive device.

Figure 2:
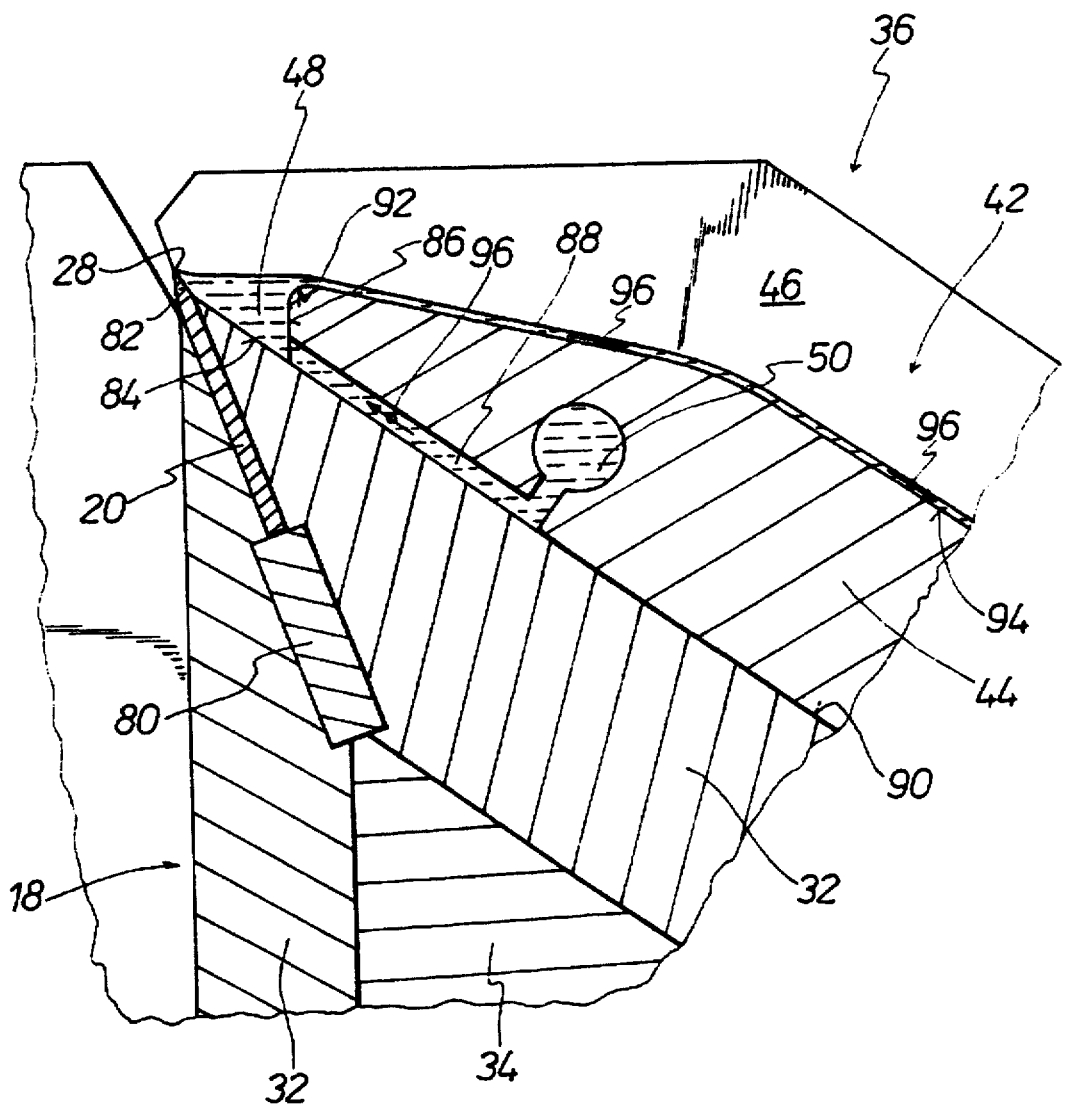
Figure 3:
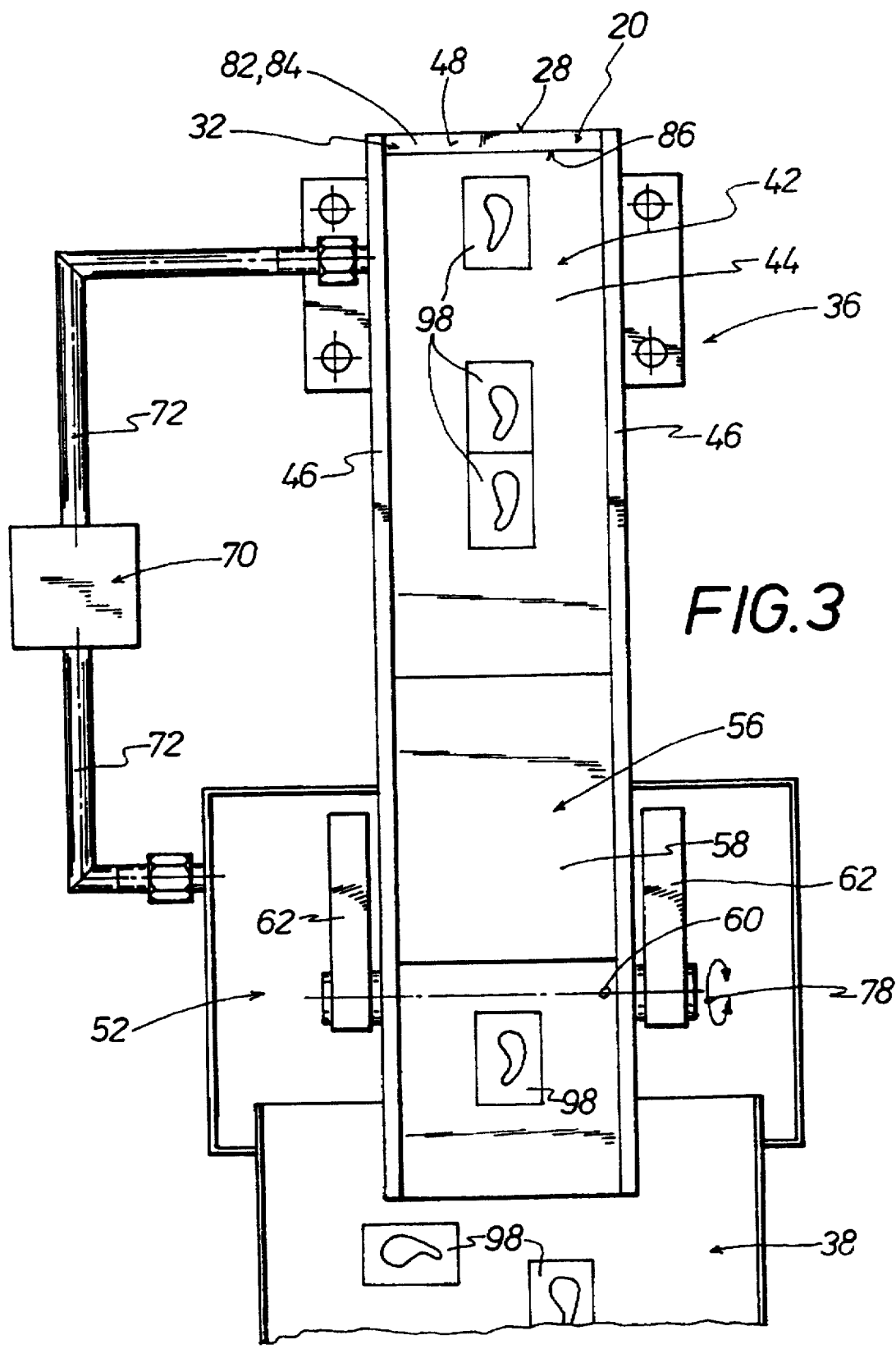
Figure 4:
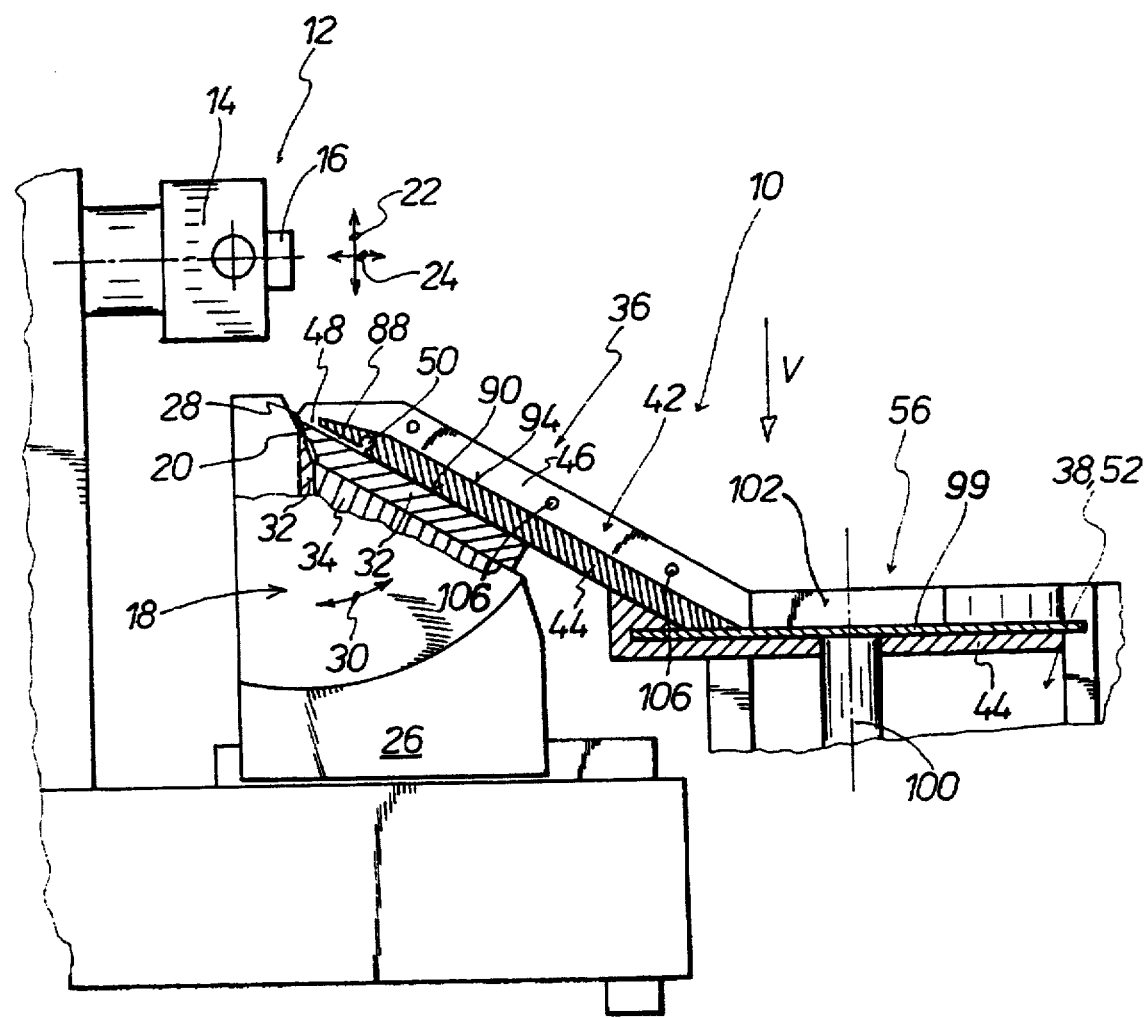
Figure 5:
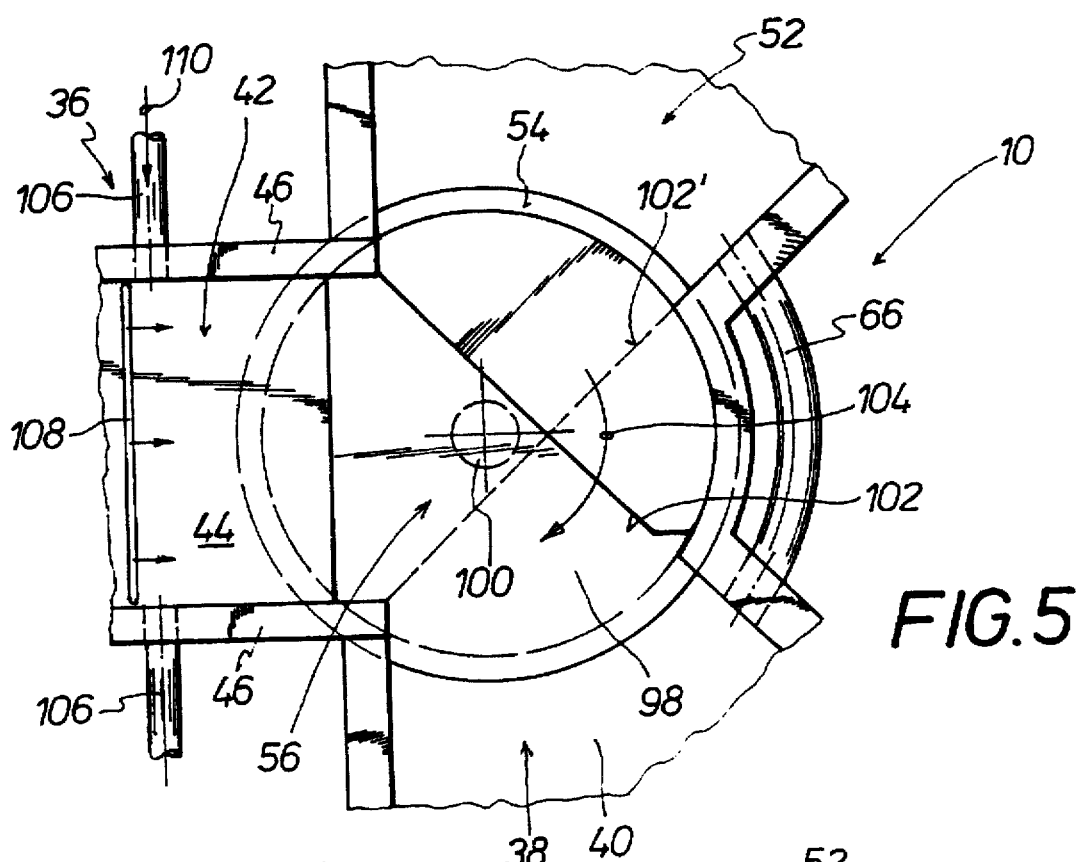
Figure 7:
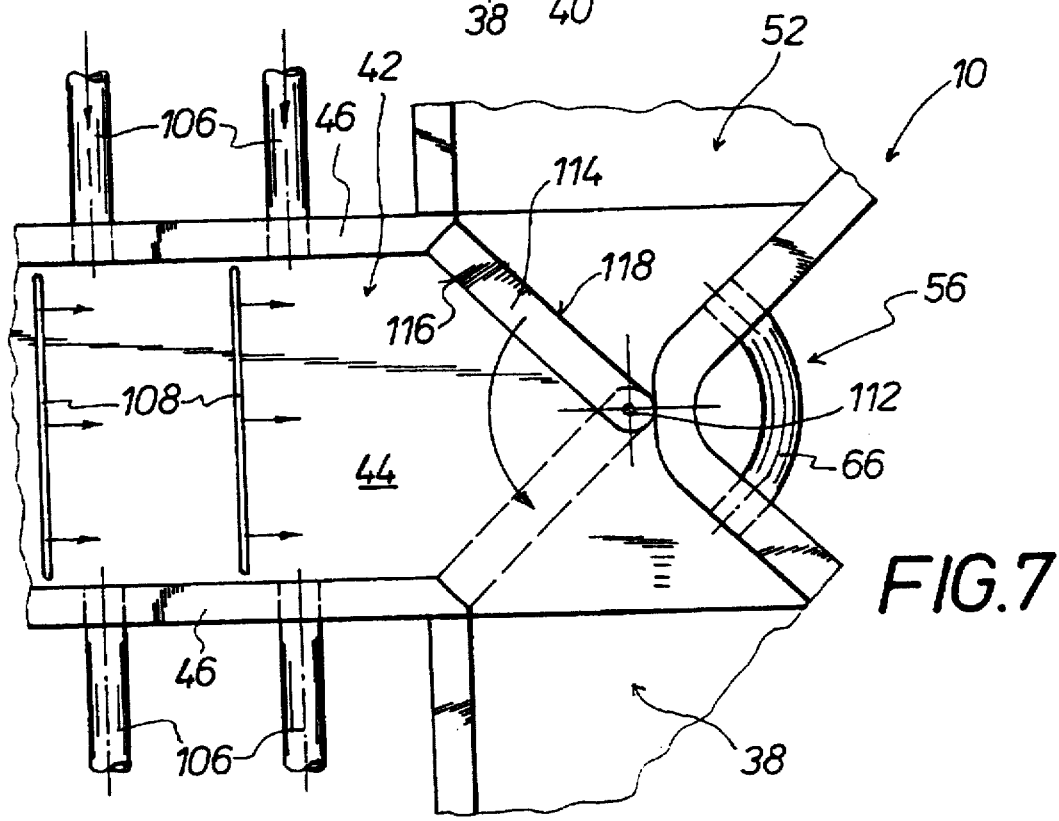
Figure 6:
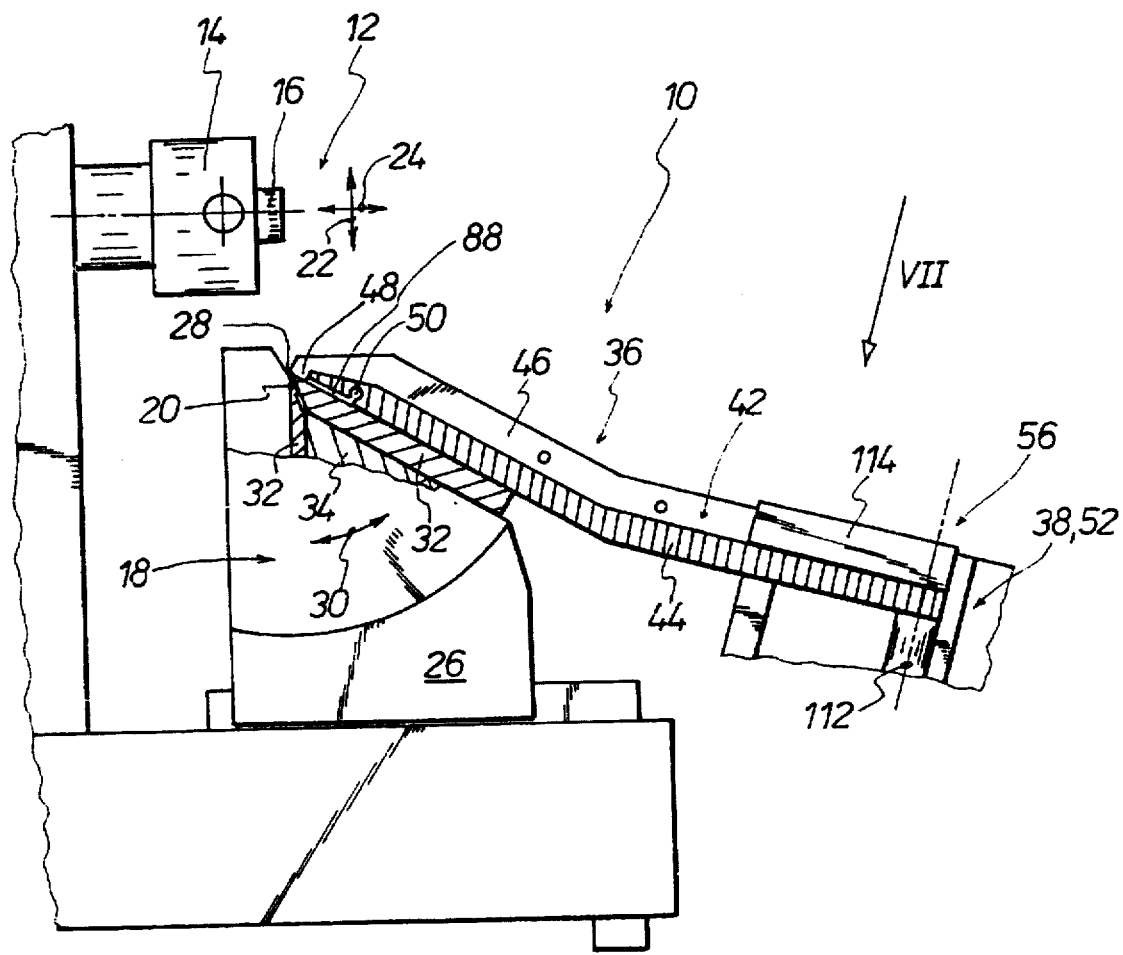
Figure 8:
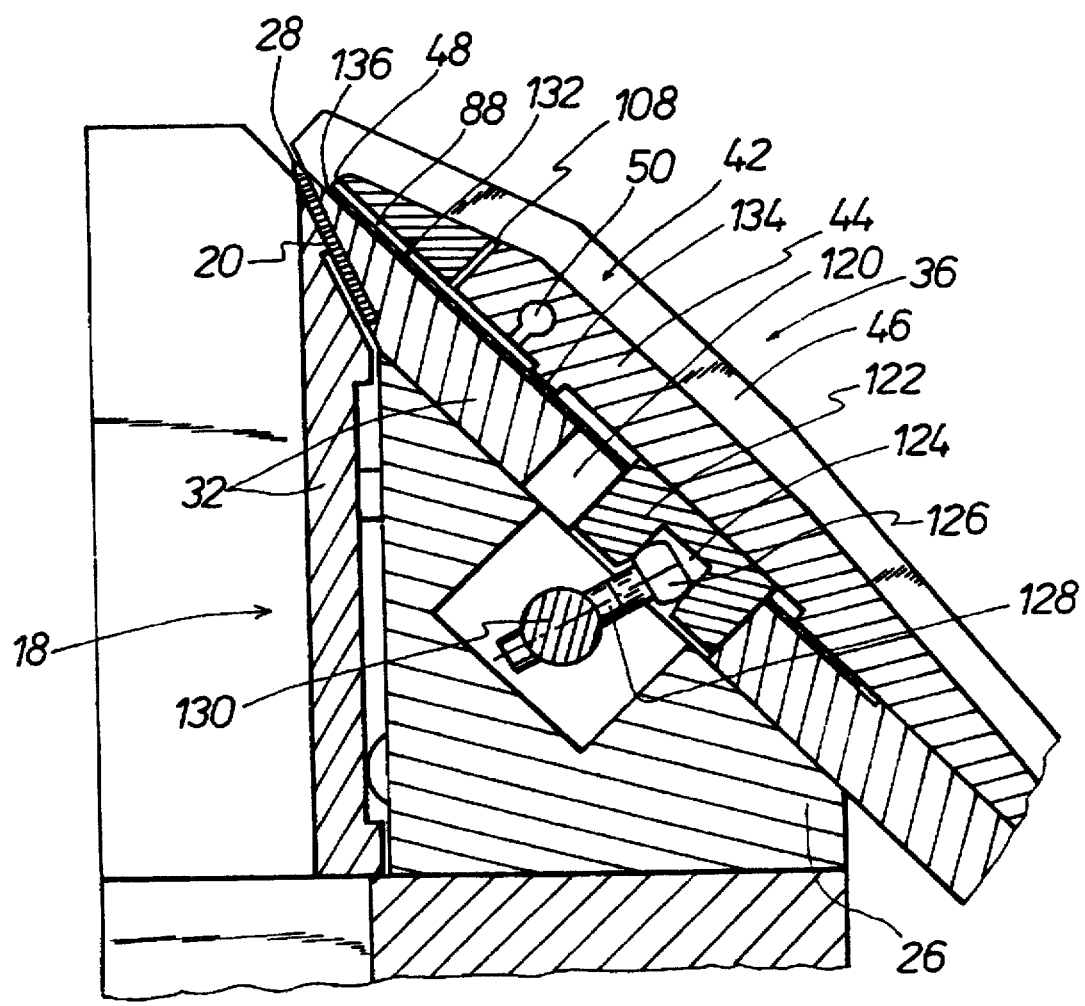

Further details, features and advantages will be apparent from the following description of embodiments of the apparatus according to the invention for carrying out the process according to the invention, as illustrated in the drawing in which:

FIG. 1 is a partly sectional side view of a first embodiment of the apparatus,

FIG. 2 is a sectional view on an enlarged scale of the detail indicated at II in FIG. 1, FIG. 3 is a view of part of the apparatus shown in FIG. 1, viewing from above in the direction indicated by the arrow III, FIG. 4 is a partly sectional side view, similar to that shown in FIG. 1, of a second embodiment of the apparatus, FIG. 5 is a view in particular of the change-over switching device shown in FIG. 4, viewing in the direction indicated by the arrow V in FIG. 4, with only parts of the flow passage, the liquid container and the waste container being shown, FIG. 6 is a partly sectional side view, similar to FIGS. 1 and 4, of the essential parts of a third embodiment of the apparatus, FIG. 7 is a plan view of essential parts of the apparatus shown in FIG. 6, viewing in the direction of the arrow VII, in particular to show the third embodiment of the change-over switching device in conjunction with the flow passage, of which part is shown, and the liquid bath of which part is shown, and the waste container, and FIG. 8 is a view in section through a blade holder for a cutting blade, in particular to show the release device disposed movably in the vicinity of the cutting blade, for releasing individual thin sections or a strip of thin sections.

FIG. 1 is a side view of part of an apparatus 10 with a microtome 12 of which a portion is shown and which comprises a specimen holder 14 for fixing a thin-section specimen 16 from which thin sections are to be cut, and a blade holder 18 for fixing a cutting blade 20. The specimen holder 14 and the cutting blade 20 are movable relative to each other in a first direction in space, as is shown by the double-headed arrow 22, for cutting thin sections from the specimen 16. The double-headed arrow 22 therefore represents the cutting motion. In addition the specimen holder 14 and the cutting blade 20 are displaceable relative to each other in a second direction in space, which is perpendicular to the first direction 22, as indicated by the double-headed arrow 24. The double-headed arrow 24 therefore shows the feed movement by which the cutting thickness, that is to say the thickness of the individual thin sections which are cut from the specimen 16, is adjusted. In addition, the blade holder 18 can be pivoted about the cutting edge 28 of the cutting blade, in relation to a base part 26 of the microtome 12, as indicated by the arcuate double-headed arrow 30. In that way, the cutting angle of the cutting blade 20 in relation to the specimen 16 from which thin sections are to be cut can be adjusted.

The blade holder 18 which is not subject-matter of the present invention has for example two clamping jaw elements 32 for clamping fast the cutting blade 20. The jaw elements 32 are disposed adjustably on a wedge-shaped base portion 34. Provided on the base portion 34 or on the blade holder 18 is an arrangement 36 which makes a fluid communication between the cutting blade 20 or between the portion of the cutting blade 20 which directly adjoins the cutting edge 18, and a bath container 38 for the liquid bath 40. For that purpose the arrangement 36 is provided with a flow passage 42 which has a bottom 44 and two spaced-apart side walls 46 which stand away from the bottom 44 in the same direction. In the immediate vicinity of the cutting edge 28 of the cutting blade 20, the arrangement 36 is provided with a cavity 48 which will be described in greater detail hereinafter with reference to FIG. 2. The cavity 48 is in fluid communication with a collecting space or chamber 50 which itself is in fluid communication with a waste container 52. The waste container 52 is arranged below an outlet 54 which is formed in the arrangement 36 and above which is disposed a change-over switching device 56. In the embodiment shown in FIG. 1, the switching device 56 has a flap 58 which is displaceable about a pivot axis 60 parallel to the bottom 44 of the flow passage 42, between a first position which is shown hatched and in solid lines in this Figure, and a second position which is shown by thin broken lines. For that purpose, the flap 58 may be connected to at least one pivot lever 62 disposed laterally beside the arrangement 36.

When the flap 58 of the change-over switching device 56 is in the position shown in hatching and with solid lines, a fluid communication is formed between the bath container 38 and the cavity 48 provided in the vicinity of the cutting edge 28 of the cutting blade 20, so that thin sections which are cut from the specimen 16 are passed into the liquid bath 40 in the bath container 38 by means of a fluid which flows through the flow passage 42 to the bath container 38. Those thin sections are so-called good thin sections which are then removed in known manner from the liquid bath 40, on the surface 64 of which they float. The bath container 38 has an overflow means 66 through which excessive liquid is transferred from the bath container 38 to the waste container 52. From the waste container 52, the liquid 68 is then conveyed back to the collecting space or chamber 50, which is effected by means of a conveyor device 70 as is diagrammatically shown in FIG. 3. The conveyor device 70 is desirably a conveyor pump. In addition, FIG. 3 shows a conduit 72 in which the conveyor device 70 is disposed and which provides a fluid communication between the waste container 52 and the collecting chamber 50 (see FIG. 1).

In order to prevent blockage of the conduit 72 or the conveyor device 70 in the conduit 72, with thin sections, the waste container 52 is provided for example with a sieve or filter device 74 which is disposed above the level of liquid 76 in the waste container 52. Thin section specimens then come to lie on the filter device 74 when the change-over switching device 56, that is to say the flap 58, is pivoted from the position shown in hatching and with solid lines, into the position indicated by thin broken lines. More specifically, in that situation, the fluid communication between the bath container 38 and the cavity 48 which is disposed in the vicinity of the cutting edge 28 of the cutting blade 20 is interrupted and a fluid communication is made between the cavity 48 and the waste container 52, through the outlet 54.

The pivotal movement of the flap 58 about the pivot axis 60 is indicated in FIG. 1 by the double-headed arrow 78.

FIG. 2 is a view on a greatly enlarged scale of part of the blade holder 18 with the wedge-shaped base portion 34 on which are disposed the two clamping jaw elements 32 which serve to clamp fast a cutting blade 20. The cutting blade 20 bears for example against a support member 80 and projects with its cutting edge 28 beyond the clamping jaw elements 32.

The arrangement 36 which forms a flow passage 42 is arranged at the clamping jaw element 32 which is disposed at the front side, that is to say which is towards the bath and waste containers. The flow passage 42 is defined by the bottom 44 and by the two spaced-apart side walls 46 which project from the bottom 44 in the same direction.

The arrangement 36 is provided with the cavity 48 in the immediate vicinity of the cutting blade 20 or the cutting edge 28 thereof. The cavity 48 is defined and delimited on the one hand by the cutting edge 28 of the cutting blade 20 and the immediately adjoining back 82 of the cutting edge of the cutting blade 20 and the adjoining front portion 84 of the front clamping jaw element 32, and on the other hand, by a suitably shaped front edge 86 of the bottom 44 of the arrangement 36. Spaced-apart passages 88 which are formed at the underside 90 of the bottom 44 of the arrangement 36 open at the front edge 86. The passages 88 are in fluid communication with the chamber 50 which extends in the transverse direction in the bottom 44.

The front edge 86 of the bottom 44 of the arrangement 36 is defined at its top side by an edge portion 92. The arrangement 36 is secured to the front clamping jaw element 32 in such a way that the last-mentioned edge portion 92 is disposed beneath the cutting edge 28 of the cutting blade 20. That configuration provides for a flow of a fluid from the collecting chamber 50 through the passages 88 to the cavity 48 and from there along the top side 94 of the downwardly inclined bottom 44 of the arrangement 36, that is to say along the flow passage 42. That flow of fluid is indicated by the arrows 96 in FIG. 2. Preferably, that flow is a laminar flow which serves to transport thin sections away from the cutting blade 20 either to the bath container 38 (see for example FIG. 1) or to the waste container 52. The flow of fluid prevents compression or buckling of the individual thin sections, while at the same time producing a stretching effect in respect thereof.

FIG. 3 is a view from above of the cutting edge 28 of the cutting blade 20, and the front edge 86 of the bottom 44 of the arrangement 86, which is defined by two side walls 46. The cavity 48 is defined by the front edge 86 of the bottom 44 of the arrangement 36, and by the front portion 84 of the front clamping jaw element 32 and also the back 82 of the cutting edge of the cutting blade 20. The cavity 48 forms so-to-speak a fluid source for the flow passage 42. That fluid source is supplied with fluid through the conduit 72.

Disposed in the flow passage 42 is the change-over switching device 56 which, in this embodiment, as is apparent from FIG. 1, comprises a flap 58 which is pivotable about the pivot axis 60. For that purpose the flap 58 is connected to two lateral pivot levers 62 so that operation is possible both with the right hand and with the left hand. The pivotal movement of the flap 58, that is to say actuation of the switching device 56, is also indicated in FIG. 3 by the double-headed arrow 78. FIG. 3 shows the switching device 56 in the position in which the thin sections 98 are passed through the flow passage 42 into the bath container 38. The bath container 38 is in fluid communication by means of an overflow 66 (see also FIG. 1) with the waste container 52 from which the conduit 72 discharges. Therefore, the fluid which flows along the flow passage 42, preferably with a laminar flow, is always in a closed circuit, that is to say, irrespective of the switching device 56 being in one or other of the possible positions. The loss of fluid which in this case is therefore the liquid in the waste container 52 and in the bath container 38 is negligibly low.

FIGS. 4 and 5 show a second embodiment of the apparatus 10, the same components being identified in these Figures by the same references as in FIGS. 1, 2 and 3, so that there is no need for all such features to be described in detail once again here. FIGS. 4 and 5 serve in particular to clearly show the second embodiment of the change-over switching device 56 in the flow passage 42 of the arrangement 36. In this embodiment the change-over switching device 56 has a plate or turntable 99 which is connected to a shaft 100. The shaft 100 is oriented perpendicularly relative to the flow passage 42. A deflection surface 102 projects from the turntable 99.

It will be seen from FIG. 5 that the turntable 99 is pivotable between a position shown in solid lines and a position indicated by a thin broken line, such pivotal movement being indicated by the arrow 104. When the deflection surface 102 is in the position shown in solid lines, the flow passage 42 is in fluid communication with the bath container 38, of which a part is shown, containing the liquid bath 40. When the deflection surface 102 is in the position shown in thin broken lines, as indicated at 102', the flow passage 42 is in fluid communication with the waste container 52 of which a portion is shown. In this embodiment of the apparatus 10, the bath container 38 is also communicated with the waste container 52 through an overflow means 66. The waste container 52 is itself once again in fluid communication with the collecting chamber 50 (see FIGS. 1, 2 and 4) by means of a conduit 72 (see FIG. 3).

FIG. 5 also shows parts of two laterally oppositely disposed fluid inlets 106 which open into the side walls 46 of the flow passage 42. Also illustrated is a fluid inlet 108 provided in the bottom 44 of the flow passage 42. The fluid inlets 106 and 108 are also in fluid communication with the waste container 52 by means of conduits (not shown) in which valve devices may be provided. In that arrangement, a suitable proportion of the fluid may be permanently introduced through the slot-shaped fluid inlets 108 in the bottom 44 of the flow passage 42, while the introduction of a suitable proportion of the fluid through the fluid inlets 106 is desirably selected in dependence on the respective position of the turntable 99 of the switching device 56. When the deflection surface 102 is in the position shown in solid lines, a suitable proportion of the fluid is desirably introduced through the fluid inlets 106 shown at the top in FIG. 5, as indicated by the arrow 110. That produces a strengthening effect for the flow along the edge of the upper side wall 46, that is to say the side wall which is on the left in the direction of flow, and from there along the deflection surface 102 of the switching device 56, thereby providing for a good guidance action for the thin sections from the specimen 16, through the flow passage 42, to the bath container 38. When the switching device 56 has been switched over into the position of the deflection surface shown in thin broken lines, as identified by reference 102', then at the same time the flow of the corresponding proportion of fluid through the fluid inlets 106 which are shown at the top in FIG. 5 is desirably interrupted and the corresponding proportion of fluid is introduced into the flow passage 42 through the lower fluid inlets 106 which are thus disposed on the right-hand side in the direction of flow of the fluid, in order now correspondingly to strengthen the flow at the deflection surface in the position 102'. In that situation, the flow of fluid through the slot-shaped fluid inlets 108 in the bottom 44 of the flow passage 42 can remain unaltered.

FIGS. 6 and 7 show the apparatus 10 with a third embodiment of the change-over switching device 56 in the flow passage 42 of the arrangement 36 between the cutting blade 20 of the microtome 12 and the bath container 38 and the waste container 52. In this construction, the switching device 56 has a deflection finger 114 which is pivotable about an axis of rotation 112 and which is displaceable between the first position shown in solid lines in FIG. 7 and the second position shown in thin broken lines. When the deflection finger 114 is in the first position, the corresponding deflection surface 116 causes the fluid to be deflected into the bath container 38 while when the deflection finger 114 is in the second position shown in thin broken lines, the second deflection surface 118 is operative to deflect the fluid into the waste container 52. This construction of the apparatus 10 also desirably provides for controlled introduction of a suitable proportion of the fluid through the fluid inlets 106 which open into the flow passage 42 on one side and the other, in order to strengthen the flow at the deflection surface 116 or 118.

The same items are identified in FIGS. 6 and 7 by the same references as in above-described FIGS. 1 to 5, so that there is no need for all those features to be described in detail once again at this point, with reference to FIGS. 6 and 7.

FIG. 8 is a sectional view of a portion of the apparatus, showing essential parts of the blade holder 18 with a wedge-shaped main portion 26 and the two clamping jaw elements 32 which are disposed thereon and which serve to fix a cutting blade 20. The front clamping jaw element 32 which is shown on the right-hand side in FIG. 8 has a recess or opening 120 in which a member 122 is linearly movably disposed. The member 122 is provided with a recess 124 into which projects an actuating element 126 which is in the form of a portion of a ball. A shaft portion 128 projects away from the actuating element 126 and is fixed to a spindle 130. Pivot or actuating levers (not shown) may be provided on the spindle 130 laterally outside of the blade holder 18; it is however also possible for the spindle 130 to be provided with a suitable drive device so that an oscillating pivotal movement of the spindle 130 produces a linearly oscillating movement of the member 122 in the opening or recess 120. The member 122 extends without play through a plate 134 of a release device 132. The release device 132 is disposed in such a way that, with the front edge 136 of the plate 134, it can move towards the cutting edge 28 of the cutting blade 20 and back again from same. The release device 132 thus serves to release the rearward or trailing edge of the thin section or the rearward or trailing edge of the last thin section in a series thereof.

FIG. 8 also shows the collecting chamber 50 which is disposed in the bottom 44, the passages 88 which provide a fluid communication between the collecting chamber 50 and the cavity 48, and a slot-shaped fluid inlet 108 which extends through the bottom 44. FIG. 8 also shows a side wall 46 of the arrangement 36, which is disposed at the side of the bottom 44, thereby defining the flow passage 42 adjoining the cavity 48, for a flow of fluid therethrough.

We claim:

1. A process for the production of thin sections from a specimen, comprising the steps of:

holding the specimen using a specimen holder of a microtome;

cutting the thin sections from the specimen via a cutting edge of a cutting blade of a microtome;

transferring the thin sections from the cutting edge to a flow passage; and flowing fluid along the flow passage for transporting the thin sections to a liquid bath downstream of the flow passage.

2. The process according to claim 1, wherein fluid flow is laminar.

3. A process for the production of thin sections from a specimen, comprising the steps of:

holding the specimen using a specimen holder of a microtome;

cutting the thin sections from the specimen via a cutting edge of a cutting blade of a microtome;

transferring the thin sections to a liquid bath from the cutting blade via a fluid flowing along a flow passage from the cutting edge of the cutting blade to the liquid bath, wherein the liquid bath is spaced from the cutting edge of the cutting blade by the flow passage; and selectively diverting the fluid to one of the liquid bath and a waste container by means of a change-over switching device.

4. A process for the production of thin sections from a specimen, comprising the steps of:

holding the specimen using a specimen holder of a microtome;

cutting the thin sections from the specimen via a cutting edge of a cutting blade of a microtome;

transferring the thin sections to a liquid bath from the cutting blade via a fluid flowing along a flow passage from the cutting edge of the cutting blade to the liquid bath, wherein the liquid bath is spaced from the cutting edge of the cutting blade by the flow passage; and selectively diverting the fluid to a waste container via a change-over switching device.

5. A process for the production of thin sections from a specimen, wherein the thin sections include a rearward edge, comprising the steps of:

holding the specimen using a specimen holder of a microtome;

cutting the thin sections from the specimen via a cutting edge of a cutting blade of a microtome;

transferring the thin sections from the cutting edge to a flow passage by means of a release device disposed beside the cutting blade, wherein the release device is displaceable in relation to the cutting edge of the blade so that movement of the release device toward the cutting blade contacts the thin sections and serves to release the rearward edge of the thin sections so that the thin sections are transferred to the flow passage from the cutting blade; and flowing fluid along the flow passage for transporting the thin sections to a liquid bath downstream of the flow passage.

6. An apparatus for the production of thin sections from a specimen, comprising:

a microtome having a cutting blade and a specimen holder for holding the thin section specimen, wherein the cutting blade and the specimen holder are moveable relative to each other;

a liquid bath for receiving the thin sections from a flow passage positioned between the cutting blade and the liquid bath wherein the thin sections are transported from the cutting edge of the cutting blade to the liquid bath via the flow passage, the flow passage including a cavity defined by a portion of the cutting blade, which adjoins the cutting edge, and a front portion of a bottom portion of the flow passage, wherein at least a part of the fluid issues and flows into the flow passage from the cavity.

7. The apparatus according to claim 6, wherein the flow passage provides for a substantially laminar fluid flow.

8. The apparatus according to claim 6, wherein downstream of the cavity, the flow passage has a bottom and two mutually oppositely disposed side walls which project away from the bottom.

9. The apparatus according to claim 8, wherein the fluid is present in an amount, and wherein one of the bottom and the side walls is provided with fluid inlets for allowing adjustment of the amount of fluid in the flow passage.

10. The apparatus according to claim 8, wherein the fluid exhibits a speed of flow in the flow passage, wherein one of the bottom and side walls is provided with fluid inlets for allowing the adjustment of the speed of flow of the fluid in the flow passage.

11. The apparatus according to claim 6, further comprising a change-over switching device disposed in the flow passage for guiding the fluid to one of the liquid bath and a waste container.

12. The apparatus according to claim 11, wherein the liquid bath is provided with an overflow which opens into the waste container.

13. The apparatus according to claim 11, wherein the flow passage includes a bottom, and wherein the change-over switching device includes a flap which forms a portion of the bottom of the flow passage, the flap being pivotable about a pivot axis which is parallel to the bottom of the flow passage.

14. The apparatus according to claim 11, wherein the flow passage includes a bottom, and wherein the change-over switching device includes a turntable which is pivotable about an axis perpendicular to the bottom of the flow passage, the turntable including a face and a deflection surface which projects from the face.

15. The apparatus according to claim 11, wherein the flow passage includes a bottom, and wherein the change-over switching device includes a deflection finger which is pivotable about an axis of rotation which is perpendicular to the bottom, the deflection finger having two guide surfaces which face away from each other and which project out of the bottom of the flow passage.

16. The apparatus according to claim 15, wherein the thin sections include a last thin section having a rearward edge, further including a release device for releasing the rearward edge of the last thin section, the release device disposed beside the cutting blade in the vicinity of the cavity, wherein the release device is displaceable in relation to the cutting edge of the cutting blade.

17. The apparatus according to claim 6, further comprising a change-over switching device disposed in the flow passage for guiding the fluid to a waste container.

18. The apparatus according to claim 17, further comprising a return line for fluid communication between the waste container and the cavity and a conveyor device for conveying the fluid in the return line.

19. The apparatus according to claim 18, wherein the fluid is present in an amount, and wherein downstream of the cavity, the flow passage includes a bottom and two mutually oppositely disposed side walls which project away from the bottom, and wherein one of the bottom and the side walls include inlets for the adjustment of the amount of fluid in the flow passage, wherein the return line is connected to the fluid inlets.

* * * * *